(12) United States Patent
Wyllie

(10) Patent No.: US 7,138,405 B2
(45) Date of Patent: Nov. 21, 2006

(54) PHARMACEUTICAL COMBINATIONS

(75) Inventor: Michael G Wyllie, Kent (GB)

(73) Assignee: Novartis International Pharmaceutical Ltd, Hamilton (BM)

( * ) Notice: Subject to any disclaimer, the term of this patent is extended or adjusted under 35 U.S.C. 154(b) by 0 days.

(21) Appl. No.: 11/140,723

(22) Filed: May 31, 2005

(65) Prior Publication Data
US 2005/0222165 A1 Oct. 6, 2005

Related U.S. Application Data

(63) Continuation of application No. 09/778,290, filed on Feb. 7, 2001.

(60) Provisional application No. 60/181,310, filed on Feb. 9, 2000.

(51) Int. Cl.
A61K 31/505 (2006.01)
A61K 31/517 (2006.01)
A61K 31/405 (2006.01)
A61K 31/135 (2006.01)

(52) U.S. Cl. .................. 514/272; 514/649; 514/264.1; 514/266.2; 514/304; 514/307; 514/317; 514/415; 514/646

(58) Field of Classification Search ..................... None
See application file for complete search history.

(56) References Cited

U.S. PATENT DOCUMENTS

| 2,503,059 A | 4/1950 | Miescher et al. |
| 2,599,000 A | 6/1952 | Kerwin et al. |
| 3,381,009 A | 4/1968 | Palazzo et al. |
| 4,252,721 A | 2/1981 | Silvestrini et al. |
| 4,703,063 A | 10/1987 | Imai et al. |
| 5,096,890 A | 3/1992 | Cross et al. |
| 5,233,053 A | 8/1993 | Cross et al. |

FOREIGN PATENT DOCUMENTS

| WO | WO 9409785 | 5/1994 |
| WO | WO 9830560 | 7/1998 |
| WO | WO 0121167 | 3/2001 |

OTHER PUBLICATIONS

Barry et al., J. Urol., vol. 148, pp. 1549-1557, (1992).
J.P. Hieble, et al., vol. 30, 1995, pp. 269S-298S, "Recent Progress in the Pharmacotherapy of Diseases of the Lower Urinary Tract".
Journal of Urology, 1985, vol. 134, pp. 1291-1298.
Kenny, et al., Urol., vol. 44, pp. 52-57, (1997).
Serels, S., and Stein, M., Prospectice Study comparing hyoscyamine, doxazosin, and combination therapy for the treatment of urgency and frequency in women, Nuerourological Urodynamics, vol. 17(1), pp. 31-36, 1998 (Abstract).
Tohoku J. Exp. Med., 1993, 170, 251-260, Effects of Intravesically Adminstered Anticholinergics, and β-Adrenergic Stimulant and α-Adrenergic Blocker on Bladder Function in Unanestgetized Rats.
Wallis et al., Life Sci., vol. 64, pp. 395-401, (1999).

Primary Examiner—Dwayne Jones
(74) Attorney, Agent, or Firm—Peter J. Waibel; Edward J. Wilusz

(57) ABSTRACT

Pharmaceutical combinations suitable for treating the lower urinary tract symptoms (LUTS) associated with benign prostatic hyperplasia (BPH) in men are described herein. The combinations contain an alpha-adrenoceptor antagonist and a muscarinic antagonist that may be administered simultaneously, separately or sequentially. The methods of treatment using the combinations are particularly suitable for treating moderate or severe LUTS.

11 Claims, No Drawings

PHARMACEUTICAL COMBINATIONS

This application is a continuation of patent application Ser. No. 09/778,290, filed Feb. 7, 2001 which is a Non-Provisional of Provisional 60/181,310, filed Feb. 9, 2000, which in their entirety are herein incorporated by reference.

FIELD OF THE INVENTION

This invention relates to pharmaceutical combinations suitable for treating the lower urinary tract symptoms (LUTS) associated with benign prostatic hyperplasia (BPH) in men, which combinations contain an alpha-adrenoceptor antagonist and a muscarinic antagonist. The combinations of the invention are particularly suitable for treating moderate or severe LUTS.

BACKGROUND

BPH is a progressive, nearly universal condition in aging men characterized by a nodular enlargement of prostatic tissue resulting, through obstruction of the urethra, in variable degrees of bladder outlet obstruction. The disorder is not a major cause of death, but it is a leading cause of morbidity in elderly men and is associated with a variety of lower urinary tract symptoms. LUTS in males include, inter alia, increased frequency of urination, nocturia, a poor urine stream and hesitancy or delay in starting the urine flow. Chronic consequences of BPH can include hypertrophy of bladder smooth muscle, a decompensated bladder and an increased incidence of urinary tract infection. The specific biochemical, histological and pharmacological properties of the prostate adenoma leading to the bladder outlet obstruction are not yet known. However, the development of BPH is considered to be an inescapable phenomenon for the aging male population. BPH is commonly seen in men over the age of 50 and is observed in approximately 70% of males over the age of 70. Currently, in the United States, the method of choice for treating BPH is the administration of $alpha_1$-adrenoceptor antagonists and, to a lesser extent, surgery, usually involving transurethral resection of the prostate (TURP). The limitations of surgery for treating BPH include the morbidity associated with an operative procedure in elderly men, persistence or recurrence of obstructive and irritative symptoms, as well as the significant cost of surgery. In general, $alpha_1$-adrenoceptor antagonists are used only in the treatment of patients with mild or moderate LUTS.

LUTS are recognized as arising from changes in urethral resistance induced by the enlarging prostate; the outflow of urine is restricted and secondary changes are induced in the bladder. A characteristic pattern of unstable bladder contractions, also known as irritable bladder, is often observed in men with morphological BPH.

Although LUTS can arise from many causes, abnormally high activity in the sympathetic nervous system is considered a prime determinant. Noradrenaline, a neurotransmitter released from sympathetic nerve terminals, contracts the prostatic smooth muscle that surrounds the urethra, increases urethral resistance and thereby reduces uroflow.

Alpha-adrenergic receptors (herein also referred to as "alpha-adrenoceptors" or as "alpha-receptors") are specific protein recognition sites loaded in the peripheral and central nervous systems and other tissues throughout the body. Neurotransmitters, such as noradrenaline, control many physiological processes via an action on these receptors and thereby transmit information between cells or influence cells or influence biochemical processes within the cell. Many agents capable of modifying noradrenaline activity on alpha-adrenoceptors have been developed over the last 40 years. Drugs active at alpha-adrenoceptors can be broken down into two major classes, agonists and antagonists. Agonists, of which phenylephrine and methoxamine are examples, activate the receptor system in the same way as the endogenous neurotransmitters, adrenaline and noradrenaline. Antagonists, of which phenoxybenzamine and prazosin are examples, do not activate the receptor, but block the actions of the endogenous neurotransmitters.

Different alpha-adrenoceptor types have been discovered over the years including $alpha_1$-adrenoceptors and $alpha_2$-adrenoceptors. These receptor types are now considered to be subdivided further into subtypes including $alpha_{1A}, _{1B}, _{1D}, _{1H}, _{1L}$ and $_{1N}$.

$Alpha_1$-adrenoceptors are known to mediate the contraction of vascular (arterial and venous) and prostatic smooth muscle. $Alpha_1$-adrenoceptor antagonists have been widely used as first line therapy for the treatment of hypertension and, more recently, for the symptomatic relief of BPH (see Kenny et al, Expert Opin in Invest Drugs, 1995, 4, 915–923).

Alpha-adrenoceptor antagonists are known to relieve the obstruction by causing relaxation of the prostate smooth muscle, a decrease in urethral resistance and increased uroflow. As a result of these changes, male patients with the clinical symptoms of mild-moderate BPH experience a moderate improvement in symptoms. The magnitude of the effect is considerably less than that achieved after surgery.

LUTS, although traditionally associated with BPH, can be found in both men and women. It is noted that women, although they of course do not develop morphological BPH, also suffer due to unstable bladder contractions. The clinical symptoms, particularly frequency and urgency, are similar in women and men.

Bladder excitability is under control of the parasympathetic nervous system that releases the neurotransmitter acetylcholine. Acetylcholine acts on protein recognition sites in the bladder called antimuscarinic receptors, producing an increase in electrical excitability of the bladder and concentration of bladder muscle. Unstable bladder is known to arise due to abnormal excitability or contractility.

Drugs active at muscarinic receptors can be broken into two major classes, agonists and antagonists. Agonists activate the receptor system in the same way as the endogenous neurotransmitter acetylcholine. Muscarinic antagonists (herein referred to as "antimuscarinics", of which atropine and hyoscine are examples) do not activate the receptor, but block the actions of the endogenous transmitter. Different muscarinic receptor types have been discovered over the years including $M_1$, $M_2$ and $M_3$.

Antimuscarinic-agents are known to relieve many of the symptoms arising from unstable or irritable bladder in women experiencing urinary urge incontinence. The combination of Hyoscyamine and Doxazosin has also been found to be efficacious in treating these symptoms in women (see, e.g., Serels, S., et al., *Neurourology and Urodynamics*, 17, 31–36 (1998)). However, in normal circumstances, the LUTS arising from BPH-induced unstable bladder contractions in men, should not be treated with antimuscarinics. Indeed the use of antimuscarinics in the treatment of LUTS in men with BPH is contraindicated as urinary retention, requiring catheterization or surgery, may result (see, M. Caine, et al., *Br. J. Urol.*, 47(2), 193–202 (1975))

SUMMARY

The present invention provides a combination of an alpha-adrenoceptor antagonist and a muscarinic antagonist for use as a medicament. In particular, it teaches the use of an alpha-adrenoceptor antagonist in combination with a muscarinic antagonist in the manufacture of a medicament for treating the lower urinary tract symptoms associated with benign hyperplasia in mammals. In one embodiment, the medicament (or product) includes a first pharmaceutically acceptable composition containing an alpha-adrenoceptor antagonist and a second pharmaceutically acceptable composition containing a muscarinic antagonist wherein the product is a combined preparation for simultaneous, separate or sequential use of the first composition and the second composition.

In another embodiment of the present invention, a pharmaceutical composition is provided which comprises an alpha-adrenoceptor antagonist, a muscarinic antagonist and a pharmaceutically acceptable carrier. The composition may be used in the treatment of lower urinary tract symptoms associated with benign hyperplasia in mammals.

In yet another embodiment of the present invention, a method of treating the lower urinary tract symptoms associated with benign prostatic hyperplasia is provided which includes administering to a subject (or mammal) in need thereof an effective amount of an alpha-adrenoceptor antagonist in combination with a muscarinic antagonist. The combination may be administered separately, simultaneously or sequentially.

DETAILED DESCRIPTION

Reference to an alpha-adrenoceptor antagonist and/or to a muscarinic antagonist, both in this disclosure and the appendant claims, shall at all times be understood to include all active forms of such agents, including the free form thereof (e.g. the free and/or base form) and also all pharmaceutically acceptable salts, polymorphs, hydrates, silicates, stereoisomers, (e.g. diastereisomers and enantiomers) and so forth. Active metabolites of either the alpha-adrenoceptor antagonist or the muscarinic antagonist, in any form, are also included.

The alpha-adrenoceptor antagonist can be selective for $alpha_1$-adrenoceptors or it can be non-selective, exhibiting antagonist activity at both the $alpha_1$ and $alpha_2$ receptors. Antagonists selective for the $alpha_1$-adrenoceptor are preferred. In the context of the known $alpha_1$-adrenoceptor subtypes, antagonists at $_{1A}$, $_{1B}$, $_{1D}$, $_{1H}$, $_{1N}$ and $_{1L}$ are equally preferred.

Suitable $alpha_1$-adrenoceptor antagonists include 4-amino-6,7-dimethoxy-2-(5-methanesulfonamido-1,2,3,4-tetrahydroisoquinol-2-yl)-5-(2-pyridyl)quinazoline (as described in example 19 of WO 98/30560), alfuzosin, indoramin, maftopidil, tamsulosin, doxazosin, terazosin, abanoquil, prazosin and pharmaceutically acceptable salts thereof. Preferred $alpha_1$-adrenoceptor antagonists include 4-amino-6,7-dimethoxy-2-(5-methanesulfonamido-1,2,3,4-tetrahydroisoquinol-2-yl)-5-(2-pyridyl)quinazoline, doxazosin, terazosin, indoramin, abanoquil, and prazosin, and the pharmaceutically acceptable salts thereof (especially doxazosin mesylate, terazosin hydrochloride, abanoquil mesylate and prazosin hydrochloride)

Further alpha-adrenoceptor antagonists which are reported to be selective for the $alpha_1$ receptor include: Recordati 15/2739, SNAP 1069, SNAP 5089, RS 17053 and SL 89.0591 (Kenny, et al., *Expert Opin in Invest Drugs*, 4, 915–923 (1995)).

Suitable non-selective alpha-adrenoceptor antagonists include phentolamine, trazodone, dapiprazole and phenoxybenzamine.

The alpha-adrenoceptor antagonists useful in this invention may be widely chosen from among those already known to the art or subsequently discovered and/or hereafter discovered and/or hereafter developed. In addition to those specifically identified above, alpha-antagonists and salts thereof have been widely disclosed in the patent literature, including U.S. Pat. Nos. 5,599,810; 5,340,814; 5,508,279; 4,755,507; 4,188,390; 4,026,894; 3,511,836; 4,315,007; 3,527,761; 3,997,666; 2,503,059; 4,703,063; 3,381,009; 4,252,721 and 2,599,000, each of which is incorporated herein by reference.

The alpha-adrenoceptor antagonism of a compound, and therefore its suitability for use in the present invention, can be determined using a number of conventional assays in vitro. Suitable assays include those disclosed in U.S. Pat. No. 5,599,810 which uses rabbit aorta to determine $alpha_1$-adrenoceptor antagonist activity and U.S. Pat. No. 5,340,814 which employ rat brain cortex to determine antagonist activity. Both of these patents are incorporated herein by reference.

The muscarinic antagonist can be selective for $M_3$ receptors or it can be non-selective, exhibiting antagonism at $M_1$, $M_2$ and $M_3$. Antagonists selective for the $M_3$ receptor are preferred.

Suitable $M_3$ receptor selective muscarinic antagonists are darifenacin and pharmaceutically acceptable salts thereof.

Suitable non-selective muscarinic antagonists include atropine, fluvoxate, hyoscine, oxybutynin, tolterodine, propantheline, propiverine, trospium and the pharmaceutically acceptable salts thereof.

Of the foregoing, darifenacin, tolterodine and oxybutynin and pharmaceutically acceptable salts thereof are especially preferred, particularly darifenacin citrate.

The muscarinic antagonists useful in this invention may be widely chosen from among those already known to the art or subsequently discovered and/or hereafter discovered and/or hereafter developed. In addition to those specifically identified above, pyrrolidine antimuscarinic antagonists have been disclosed in the patent literature, including U.S. Pat. Nos. 5,233,053 and 5,096,890, both of which are incorporated herein by reference.

The muscarinic antagonist activity of a compound, and therefore its suitability for use in the present invention, can be determined using a number of conventional assays in vitro (see, Wallis and Napier, *Life Sci*, 64, 395–401, (1997)).

A suitable combination is a muscarinic antagonist and a non-selective alpha-adrenoceptor antagonist.

Preferred combinations are a muscarinic antagonist with a selective $alpha_1$-adrenoceptor antagonist and a non-selective alpha-antagonist with a muscarinic antagonist that is selective for the $M_3$ receptor.

A more preferred combination is a selective $alpha_1$-adrenoceptor antagonist and a muscarinic antagonist that is selective for the $M_3$ receptor subtype. The most preferred is the combination of any alpha-adrenoceptor antagonist with darifenacin.

Preferred specific combinations include doxazosin with darifenacin; 4-amino-6,7-dimethoxy-2-(5-methanesulfonamido-1,2,3,4-tetrahydroisoquinol-2-yl)-5-(2-pyridyl) quinazoline and darifenacin; and pharmaceutically acceptable salts thereof.

Administering both therapeutic agents produces an effect that is greater than that of the alpha-adrenoceptor antagonist administered alone. This is advantageous in that it allows for a smaller amount of the alpha-adrenoceptor antagonist to be administered to provide a therapeutic effect. A further advantage is that therapy can be effected for patients who, for example, do not respond adequately to the use of the alpha-adrenoceptor antagonist at what would be considered a maximal strength dose.

According to one aspect of the present invention, there is provided a product (medicament) comprising a first pharmaceutically acceptable composition containing an alpha-adrenoceptor antagonist and a second pharmaceutically acceptable composition containing a muscarinic antagonist for use as a combined preparation for simultaneous, separate or sequential use in treating the lower urinary tract symptoms associated with benign hyperplasia in mammals.

In one embodiment, the alpha-adrenoceptor antagonist in the first composition is non-selective. Preferably the alpha-adrenoceptor antagonist in the first composition is selective for $\alpha_1$ receptors. More preferably the alpha$_1$-adrenoceptor antagonist in the first composition is selected from 4-amino-6,7-dimethoxy-2-(5-methanesulfonamido-1,2,3,4-tetrahydroisoquinol-2-yl)-5-(2-pyridyl)quinalzoline, doxazosin, tetrazosin, abanoquil, prazosin and indoramin and pharmaceutically acceptable salts thereof.

The muscarinic antagonist in the second composition may be non-selective. Preferably the muscarinic antagonist in the second composition is selected from darifenacin, tolterodine and oxybutynin and pharmaceutically acceptable salts thereof. More preferably the muscarinic antagonist in the second composition is selective for $M_3$ receptors. Most preferably the muscarinic antagonist in the second composition is darifenacin and pharmaceutically acceptable salts thereof.

The present invention provides for the administering of each of the antagonists separately but as part of the same therapeutic treatment program or regimen, and it is contemplated that separate administration of each compound, at different times and by different routes, will sometimes be recommended. Thus the two components need not necessarily be administered at essentially the same time. In the preferred embodiment the alpha-adrenoceptor antagonist will be given several days prior to initiation of the muscarinic antagonist either daily or "on demand". In another preferred embodiment, administration is timed so that the peak pharmacokinetic effect of the alpha$_1$-adrenoceptor antagonist precedes the peak pharmacokinetic effect of the muscarinic antagonist. If co-administered separately, it is also preferred that both components be administered in an oral dosage form.

The product may comprise a kit. The kit may comprise a container for containing the separate compositions such as a divided bottle or a divided foil packet, wherein each compartment contains a plurality of dosage forms (e.g., tablets) comprising either the alpha$_1$-adrenoceptor antagonist or the muscarinic antagonist.

Alternatively, rather than separating the active ingredient-containing dosage forms, the kit may contain separate compartments each of which contains a whole dosage which comprises separate compositions. An example of this type of kit is a blister pack wherein each individual blister contains two tablets, one tablet comprising the alpha-adrenoceptor antagonist, the other comprising the muscarinic antagonist.

Typically the kit comprises directions for the administration of the separate components. Such instructions would cover situations such as:

i) the dosage form in which the components are administered (e.g. oral and parenteral), ii) when the component parts of the product are administered at different dosage intervals, or iii) when titration of the individual components of the combination is desired by the prescribing physician. The container may have deposited thereon a label that describes the contents therein and any appropriate warnings.

An example of such a kit is a so-called blister pack. Blister packs are well known in the packaging industry and are widely used for the packaging of pharmaceutical unit dosage forms such as tablets, capsules, and the like. Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses between the plastic foil and the sheet. Preferably, the strength of the sheet is such that the tablets or capsules can be removed from the blister pack by manually applying pressure on the recesses whereby an opening is formed in the sheet at the place of the recess. Tablet(s) or capsule(s) can then be removed by means of the opening.

It may be desirable to provide a memory aid on the kit, e.g., in the form of numbers next to the tablets or capsules whereby the numbers correspond with the days of the regimen during which the tablets or capsules so specified should be ingested. Another example of such a memory aid is a calendar printed on the card, e.g. as follows "First Week, Monday, Tuesday, . . . etc . . . . Second Week, Monday, Tuesday, . . . ", etc. Other variations of memory aids will be readily apparent. A "daily dose" can be a single tablet or capsule or several pills or capsules to be taken on a given day. Also a daily dose of the first compound can consist of one tablet or capsule while a daily dose of the second compound can consist of several tablets or capsules and vice versa. The memory aid should reflect this.

It is also within the scope of the present invention that both the alpha-adrenoceptor antagonist and the muscarinic antagonist may be present in a single composition. Thus according to a further aspect of the invention, there is provided a pharmaceutical composition containing an alpha-adrenoceptor antagonist, a muscarinic antagonist and a pharmaceutically acceptable carrier.

Suitable alpha-adrenoceptor antagonists include those that are non-selective. Preferably the alpha-adrenoceptor antagonist is selective for the $\alpha_1$ receptor. More preferably the alpha-adrenoceptor antagonist is selected from 4-amino-6,7-dimethoxy-2-(5-methanesulfonamido-1,2,3,4-tetrahydroisoquinol-2-yl)-5-(2-pyridyl)quinazoline, doxazosin, tetrazosin, abanoquil, prazosin and indoramin and pharmaceutically acceptable salts thereof.

Suitable muscarinic antagonists include those that are non-selective. Preferably the muscarinic antagonist is selected from darifenacin, tolterodine and oxybutynin and pharmaceutically acceptable salts thereof. More preferably the muscarinic antagonist is selective for $M_3$ receptors. Most preferably the muscarinic antagonist in the second composition is darifenacin and pharmaceutically acceptable salts thereof.

Most preferred is a composition containing a combination of any alpha-adrenoceptor antagonist with darifenacin. Preferred specific combinations include: doxazosin and darifenacin; and 4-amino-6,7-dimethoxy-2-(5-methanesulfonamido-1,2,3,4-tetrahydroisoquinol-2-yl)-5-(2-pyridyl)quinazoline and darifenacin; and pharmaceutically acceptable salts thereof.

The compositions of the present invention, both those that contain only one component and those that contain both, may be suitable for topical, oral, parenteral or rectal administration. The compositions may be formulated to provide immediate or sustained release of the therapeutic agent. Particularly suitable delayed or sustained release formulations are those disclosed in WO 97/09980.

The compounds of the invention can be administered alone but will generally be administered as an admixture with a suitable pharmaceutical excipient, diluent or carrier selected with regard to the intended route of administration and standard pharmaceutical practice.

For example, the compounds of the invention can be administered orally, buccally or sublingually in the form of tablets, capsules, ovules, elixirs, solutions or suspensions, which may contain flavoring or coloring agents, for immediate-, delayed-, modified-, sustained-, pulsed- or controlled-release applications.

Generally, tablets contain various excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included. Tablets may be manufactured by any standard tablet-making process, for example, direct compression or a wet or dry granulation process. The tablet cores may also be coated with one or more appropriate overcoats.

Solid compositions of a similar type are also employed as fillers in gelatin capsules. Preferred excipients in this regard include lactose, milk sugar, cellulose, starch or high molecular weight polyethylene glycols. For aqueous suspensions and/or elixirs, the compounds of this invention can be combined with various sweetening agents, flavoring agents, coloring agents or dyes, emulsifying agents and/or suspending agents, diluents (e.g., water, ethanol, propylene glycol, glycerin and mixtures thereof and combinations thereof.

The compounds of the invention can also be administered parenterally, for example, intravenously, intra-arterially, intraperitoneally, intrathecally, intraventricularly, intraurethrally, intrasternally, intracranially, intramuscularly or subcutaneously, or they may be administered by infusion techniques. For such parenteral administration they are best used in the form of a sterile aqueous solution which may contain other substances, for example, enough salts or glucose to make the solution isotonic with blood. If necessary, the aqueous solutions should be suitably buffered (preferably to a pH from 3 to 9). The preparation of suitable parenteral formulations under sterile conditions is readily accomplished by standard pharmaceutical techniques well-known to those skilled in the art.

For application topically to the skin, the compounds of the invention can be formulated as a suitable ointment containing the active compound suspended or dissolved in, for example, a mixture with one or more of the following: mineral oil, liquid petrolatum, white petrolatum, propylene glycol, polyoxyethylene or polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-oxtyldodecanol, benzyl alcohol and water.

The alpha-adrenoceptor antagonist and/or the muscarinic antagonist may also be used in combination with a cyclodextrin. Cyclodextrins are known to form inclusion and non-inclusion complexes with drug molecules. Formation of a drug-cyclodextrin complex may modify the solubility, dissolution rate, bioavailability and/or stability property of a drug molecule. Drug-cyclodextrin complexes are generally useful for most dosage forms and administration routes. As an alternative to direct complexation with the drug the cyclodextrin may be used as an auxiliary additive, e.g., as a carrier, diluent or solubilizer. Alpha-, beta- and gamma-cyclodextrins are most commonly used and suitable examples are described in WO 91/11172, WO 94/02518 and WO 98/55148.

Other pharmaceutical components may also be optionally included as part of the combinations useful in this invention so long as they do not interfere or adversely affect the effects of the alpha-adrenoceptor antagonist/muscarinic antagonist combination.

The exact dose of each component administered will, of course, differ depending on the specific components prescribed, on the subject being treated, on the severity of the LUTS, on the manner of administration and on the judgement of the prescribing physician. Thus, because of patient-to-patient variability, the dosages given below are a guideline and the physician may adjust doses of the compounds to achieve the treatment that the physician considers appropriate for the patient, male or female. In considering the degree of treatment desired, the physician must balance a variety of factors such as the age of the patient and the presence of other diseases or conditions (e.g. cardiovascular disease). In general, the muscarinic antagonist will be administered in a range of from 0.5 to 200 mg per day, preferably 10 to 125 mg per day, more preferably 25 mg to 100 mg per day. The alpha-adrenoceptor antagonist will generally be administered in an amount of from 0.01 mg to 50 mg per day, preferably from 0.5 to 10 mg per day.

Doxazosin, when in combination, will be administered in the range 0.25 mg to 16 mg per day, preferably 2 mg to 4 mg per day. Tolterodine will be administered twice a day in the range 0.2 mg to 2 mg per day, preferably from 0.5 mg to 1 mg per day and darifenacin will be administered in the range 0.5 mg to 5 mg twice a day, preferably 1 mg or 2 mg. All weights quoted above refer to the weight of the compounds as the free base.

Methods of preparing various pharmaceutical compositions with a certain amount of active ingredient are known, or will be apparent in light of this disclosure, to those skilled in this art. For examples of methods of preparing pharmaceutical compositions, see, *Remington's Pharmaceutical Sciences,* Mack Publishing Company, Easter, Pa., 15$^{th}$ Edition (1975).

The invention is further illustrated by the following, non-limiting examples.

EXAMPLES

Example 1

Immediate Release Doxazosin Tablet:

| Ingredient | % w/w |
| --- | --- |
| Doxazosin Mesylate | 4.05 |
| Microcrystalline Cellulose | 125.28 |
| Lactose | 66.67 |
| Sodium Starch Glycollate | 2.00 |
| Magnesium stearate | 2.00 |
| Total weight | 200.00 |

The doxazosin mesylate, microcrystalline cellulose, lactose and sodium starch glycollate were blended together, passed through a screen, then blended again. The blend was lubricated with magnesium stearate and compressed using a tablet press. The resulting tablet was then given a film coating.

Example 2

Immediate Release Darifenacin Tablet:

| Ingredient | % w/w |
| --- | --- |
| Darifenacin hydrobromide | 2.976 |
| Microcrystalline Cellulose | 131.024 |
| Calcium phosphate dibasic | 60.000 |
| Croscarmellose sodium | 4.000 |
| Magnesium stearate | 2.000 |
| Total weight | 200.000 |

The darifenacin hydrobromide, microcrystalline cellulose, lactose and sodium starch glycollate were blended together, passed through a screen, then blended again. The blend was lubricated with magnesium stearate and compressed using a tablet press. The resulting tablet was then given a film coating.

Example 3

Combination Immediate Release Darifenacin/Doxazosin Tablet:

| Ingredient | % w/w |
| --- | --- |
| Doxazosin Mesylate | 4.05 |
| Darifenacin hydrobromide | 2.976 |
| Microcrystalline Cellulose | 125.28 |
| Lactose | 63.694 |
| Sodium Starch Glycollate | 2.00 |
| Magnesium stearate | 2.00 |
| Total weight | 200.00 |

The doxazosin mesylate, darifenacin hydrobromide, microcrystalline cellulose, lactose and sodium starch glycollate were blended together, passed through a screen, then blended again. The blend was lubricated with magnesium stearate and compressed using a tablet press. The resulting tablet was then given a film coating.

Example 4

Combination Immediate Release Doxazosin/Controlled Release Darifenacin Tablet:

| Ingredient | % w/w |
| --- | --- |
| Doxazosin Mesylate | 4.05 |
| Microcrystalline Cellulose | 125.28 |
| Lactose | 66.67 |
| Sodium Starch Glycollate | 2.00 |
| Magnesium stearate | 4.00 |
| Darifenacin hydrobromide | 17.857 |
| Methylhydroxypropyl cellulose | 114.400 |
| Calcium phosphate dibasic | 65.743 |
| Total weight | 400.000 |

The doxazosin mesylate, microcrystalline cellulose, lactose and sodium starch glycollate were blended together, passed through a screen, then blended again. The blend was then lubricated with magnesium stearate.

The darifenacin hydrobromide, methylhydroxypropyl cellulose and calcium phosphate dibasic were blended together, passed through a screen, then blended again. The blend was then lubricated with magnesium stearate.

The individual blends were then compressed on a bi-layer tablet press. The resulting tablet was then given a film coating.

Example 5

Controlled Release Darifenacin Tablet:

| Ingredient | % w/w |
| --- | --- |
| Darifenacin hydrobromide | 17.857 |
| Methylhydroxypropyl cellulose | 114.400 |
| Calcium phosphate dibasic | 65.743 |
| Magnesium stearate | 2.000 |
| Total weight | 200.000 |

The darifenacin hydrobromide, methylhydroxypropyl cellulose and calcium phosphate dibasic were blended together, passed through a screen, then blended again. The blend was lubricated with magnesium stearate and compressed using a tablet press. The resulting tablet was then given a film coating.

The individual components of a combination of an alpha-adrenoceptor antagonist and a muscarinic antagonist can be tested in vivo in an anaesthetized beagle dog model (see, Kenny, et al., *Urol.* 44, 52–57 (1994) in which urethral pressure and/or bladder function are measured. However, the unexpected advantage of the combination can only be determined, and thus becomes apparent, on evaluation of symptoms, an assessment that can only be carried out in man.

The combination of an alpha-adrenoceptor antagonist and a muscarinic antagonist can be tested clinically, typically orally, in humans. Each component is administered singly at different times to a population of male patients, each component being administered in conjunction with the International Prostate Symptom Score (IPSS) questionnaire (see, Barry, et al., *J. Urol.*, 148, 1549–1563 (1992)) which evaluated patient satisfaction. By administering each component singly, it is meant that one component is administered, followed at a later time by the second component after having allowed an appropriate time for washout of the first component. After the washout period for each component administered singly, the components are co-administered in a manner such that both components co-operate pharmacokinetically, preferably such that fully effective drug plasma levels of both agents will be obtained. Co-administration is evaluated according to IPSS questionnaires mentioned above, thereby providing a basis for comparison of the effects of co-administration with that for each single administration. The efficacy of the present invention is demonstrated by the results of the IPSS questionnaire.

I claim:

1. A method for treating the lower urinary tract symptoms associated with benign prostate hyperplasia in mammals comprising administering to a mammal suffering from benign prostate hyperplasia an effective amount of an alpha-adrenoceptor antagonist selected of the group of 4-amino-6,7-dimethoxy-2-(5-methanesulfonamido-1,2,3,4-tetrahydroisoquinol-2-yl)-5-(2-pyridyl)quinazoline, alfuzosin, indoramin, maftopidil, tamsulosin, doxazosin, tetrazosin, abanoquil, prazosin, phentolamine, trazodone, dapiprazole and phenoxybenzamine or pharmaceutically acceptable salts thereof in combination with a muscarinic antagonist selected from the group of darifenacin, atropine, fluvoxate, hyoscine, oxybutynin, tolterodine, propantheline, propiverine, and trospium, or pharmaceutically acceptable salts thereof.

2. The method of claim 1 wherein said alpha-adrenoceptor antagonist and said muscarinic antagonist is are administered simultaneously.

3. The method of claim 1 wherein said alpha-adrenoceptor antagonist and said muscarinic antagonist is are administered separately.

4. The method of claim 1 wherein said alpha-adrenoceptor antagonist and said muscarinic antagonist is are administered sequentially.

5. The method of claim 1 wherein the aipha-adrenoceptor antagonist is non-selective or selective for α1 receptors.

6. The method of claim 1 wherein said alpha-adrenoceptor antagonist is selected from the group consisting of 4-amino-6,7-dimethoxy-2-(5-methanesulfonamido-1,2,3,4-tetrahydroisoquinol-2-yl)-5-(2-pyridyl)quinazoline, doxazosin, tetrazosin, abanoquil, prazosin, and indoramin or pharmaceutically acceptable salts thereof.

7. The method of claim 1 wherein said muscarinic antagonist is non-selective or selective for $M_3$ receptors.

8. The method of claim 1 wherein said muscarinic antagonist is selected from the group consisting of darifenacin, tolterodine and oxybutynin or pharmaceutically acceptable salts thereof.

9. The method of claim 1 wherein said muscarinic antagonist is darifenacin, or a pharmaceutically acceptable salt thereof.

10. The method of claim 1, wherein said alpha-adrenoceptor antagonist is doxazosin and said muscarinic antagonist is darifenacin, or pharmaceutically acceptable salts of either thereof.

11. The method of claim 1 wherein said alpha-adrenoceptor antagonist is 4-amino-6,7-dimethoxy-2-(5-methanesulfonamido-1,2,3,4-tetrahydroisoquinol-2-yl )-5-(2-pyridyl)quinazoline and said muscarinic antagonist is darifenacin, or pharmaceutically acceptable salts of either thereof.

\* \* \* \* \*